(12) United States Patent

Lecamwasam et al.

(10) Patent No.: US 12,616,787 B2

(45) Date of Patent: May 5, 2026

(54) MONITORING SYSTEM FOR CARE PROTOCOLS

(71) Applicant: Talis Clinical LLC, Streetsboro, OH (US)

(72) Inventors: Harish Lecamwasam, Scottsdale, AZ (US); Giuseppe Saracino, Gainsville, FL (US); William Murphy, Aurora, OH (US); Gary Colister, Hudson, OH (US)

(73) Assignee: TALIS CLINICAL LLC, Streetsboro, OH (US)

( * ) Notice: Subject to any disclaimer, the term of this patent is extended or adjusted under 35 U.S.C. 154(b) by 102 days.

(21) Appl. No.: 17/159,617

(22) Filed: Jan. 27, 2021

(65) Prior Publication Data

US 2021/0228794 A1 Jul. 29, 2021

Related U.S. Application Data

(60) Provisional application No. 62/966,273, filed on Jan. 27, 2020.

(51) Int. Cl.
A61M 1/36 (2006.01)

(52) U.S. Cl.
CPC ........ A61M 1/3666 (2013.01); A61M 1/3607 (2014.02); A61M 1/3656 (2014.02);
(Continued)

(58) Field of Classification Search
CPC .............. A61M 1/3607; A61M 1/3656; A61M 1/3666; A61M 1/3643; A61M 2205/18; A61M 2205/583; A61M 2230/207
See application file for complete search history.

(56) References Cited

U.S. PATENT DOCUMENTS

| | | | |
|---|---|---|---|
| 5,954,666 | A | 9/1999 | Snell |
| 6,229,536 | B1 | 5/2001 | Alexander et al. |

(Continued)

FOREIGN PATENT DOCUMENTS

| | | |
|---|---|---|
| EP | 3839960 | 6/2021 |
| JP | 2004-533662 A | 11/2004 |

(Continued)

*Primary Examiner* — Rebecca E Eisenberg
*Assistant Examiner* — Kate Elizabeth Strachan
(74) *Attorney, Agent, or Firm* — McCoy Russell LLP

(57) ABSTRACT

A monitoring system for care protocols, comprising sensors connected to electronic devices to input data from a patient, where sensors measure critical values from a patient; an interface for receiving data and allowing users to write and change process control in real time; a processor connected to the interface to receive input parameters, wherein the processor calculates output values based on the input parameters compared to the critical value to determine whether the output values are outside acceptable range; means for setting critical values, ranges of critical value, and alarm points when the critical values are outside of the range; where the interface receives critical patient parameters and the interface includes a manual input and a machine input from one or more sensors; and wherein the system calculates and monitors critical steps or values for a patient and enables the output values for monitoring or display, in real time.

16 Claims, 10 Drawing Sheets

(52) U.S. Cl.
CPC ....... *A61M 1/3643* (2013.01); *A61M 2205/18* (2013.01); *A61M 2205/583* (2013.01); *A61M 2230/207* (2013.01)

(56) References Cited

U.S. PATENT DOCUMENTS

| | | |
|---|---|---|
| 6,364,834 B1 | 4/2002 | Reuss et al. |
| 6,553,436 B2 | 4/2003 | Ando et al. |
| 6,559,868 B2 | 5/2003 | Alexander et al. |
| 7,315,825 B2 | 1/2008 | Rosenfeld et al. |
| 7,467,093 B1 | 12/2008 | Newton et al. |
| 8,000,937 B2 | 8/2011 | Zeng et al. |
| 8,149,131 B2 | 4/2012 | Blomquist |
| 8,229,760 B2 | 7/2012 | Hasan et al. |
| 8,291,337 B2 | 10/2012 | Gannin et al. |
| 8,310,336 B2 | 11/2012 | Muhsin et al. |
| 8,553,036 B2 | 10/2013 | Taylor et al. |
| 8,560,335 B2 | 10/2013 | Hertel et al. |
| 8,572,589 B2 | 10/2013 | Cataldo et al. |
| 8,660,860 B2 | 2/2014 | Wehba et al. |
| 8,674,837 B2 | 3/2014 | Gilham et al. |
| 8,730,243 B2 | 5/2014 | Wenholz et al. |
| 8,892,171 B2 | 11/2014 | Ross et al. |
| 8,990,722 B2 | 3/2015 | Gannon et al. |
| 9,095,274 B2 | 8/2015 | Fein et al. |
| 9,179,852 B2 | 11/2015 | Audet et al. |
| 9,393,366 B2 | 7/2016 | Gannon et al. |
| 9,400,874 B2 | 7/2016 | Powell et al. |
| 9,413,852 B2 | 8/2016 | Lawson et al. |
| 9,927,943 B2 | 3/2018 | Gannon et al. |
| 10,039,490 B2 | 8/2018 | Ranucci |
| 10,255,408 B2 | 4/2019 | Blomquist |
| 10,354,751 B1 | 7/2019 | McNair |
| 10,657,222 B2 | 5/2020 | Chan et al. |
| 11,030,872 B2 | 6/2021 | Chan et al. |
| 11,031,129 B2 | 6/2021 | Zaleski |
| 2004/0054294 A1 | 3/2004 | Ramseth |
| 2005/0159666 A1 | 7/2005 | Pearce et al. |
| 2005/0171815 A1 | 8/2005 | Vanderveen |
| 2007/0179806 A1 | 8/2007 | Knowlton et al. |
| 2008/0086332 A1 | 4/2008 | Hertel et al. |
| 2008/0097914 A1 | 4/2008 | Dicks |
| 2008/0316045 A1 | 12/2008 | Sriharto et al. |
| 2009/0070054 A1 | 3/2009 | Zeng et al. |
| 2011/0227739 A1 | 9/2011 | Gilham et al. |
| 2012/0035957 A1 | 2/2012 | Hanz et al. |
| 2012/0075103 A1 | 3/2012 | Powell et al. |
| 2012/0278099 A1 | 11/2012 | Kelly et al. |
| 2013/0220907 A1* | 8/2013 | Fulkerson ........... A61M 1/3451 |
| | | 210/186 |
| 2014/0046674 A1 | 2/2014 | Rosenfeld et al. |
| 2014/0142963 A1 | 5/2014 | Hill et al. |
| 2014/0222446 A1 | 8/2014 | Ash et al. |
| 2014/0249855 A1 | 9/2014 | Moore |
| 2014/0266787 A1 | 9/2014 | Tran |
| 2015/0025329 A1 | 1/2015 | Amarasingham et al. |
| 2015/0100009 A1 | 4/2015 | Bearss |
| 2015/0272487 A1* | 10/2015 | Ranucci ................. G16H 40/63 |
| | | 600/301 |
| 2016/0117446 A1 | 4/2016 | Hussam et al. |
| 2016/0246943 A1 | 8/2016 | Lake et al. |
| 2017/0102846 A1* | 4/2017 | Ebler ..................... G16H 40/67 |
| 2017/0140108 A1 | 5/2017 | Lee et al. |
| 2017/0372031 A1 | 12/2017 | Muecke et al. |
| 2018/0344919 A1* | 12/2018 | Jones ................... G09B 23/303 |
| 2019/0205002 A1* | 7/2019 | Colister ................. G16H 80/00 |
| 2020/0035366 A1 | 1/2020 | Gummireddy et al. |
| 2020/0209043 A1* | 7/2020 | Garza ................... A61M 1/155 |
| 2020/0222549 A1* | 7/2020 | Novak ............... A61K 49/0056 |
| 2020/0227148 A1 | 7/2020 | Cohen et al. |
| 2020/0230316 A1* | 7/2020 | Guerra ............. A61M 5/31568 |
| 2020/0359913 A1 | 11/2020 | Ghodrati et al. |
| 2020/0394334 A1 | 12/2020 | Bulut et al. |
| 2021/0065889 A1 | 3/2021 | Page |
| 2021/0077035 A1 | 3/2021 | Kayser et al. |
| 2021/0141786 A1 | 5/2021 | Gubau i Forné et al. |
| 2021/0151145 A1 | 5/2021 | Dunn et al. |
| 2021/0151178 A1 | 5/2021 | Singh et al. |
| 2021/0202086 A1 | 7/2021 | Cherdak |
| 2021/0225505 A1 | 7/2021 | Khare et al. |
| 2021/0233628 A1 | 7/2021 | Rentas et al. |

FOREIGN PATENT DOCUMENTS

| | | |
|---|---|---|
| JP | 2016-519806 A | 7/2016 |
| WO | 2021067485 | 4/2021 |
| WO | 2021002847 | 7/2021 |

\* cited by examiner

Figure 1:
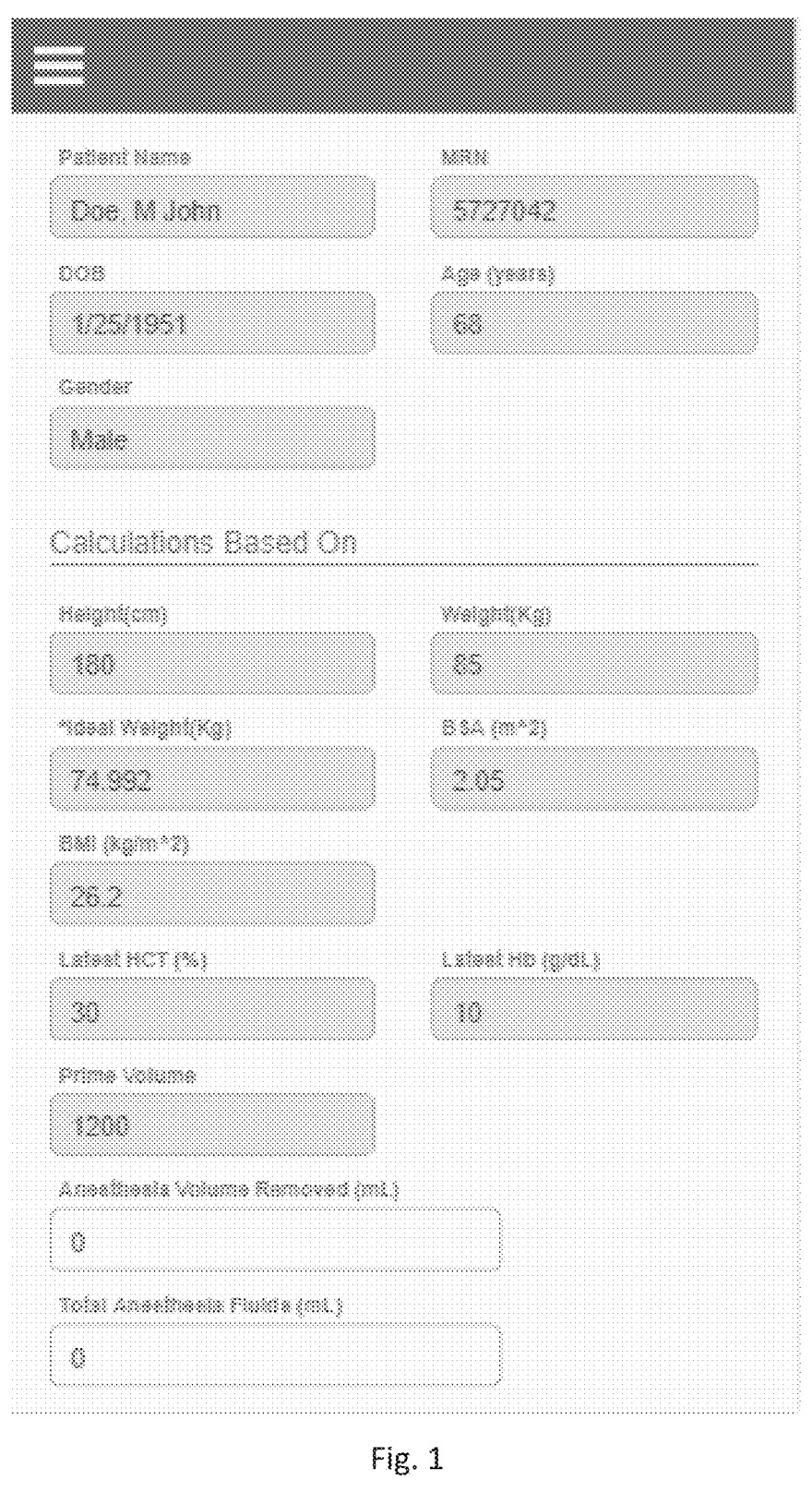

Patient Name

Doe, M John

MRN

5727042

DOB

1/25/1951

Age (years)

68

Gender

Male

Calculations Based On

Height(cm)

180

Weight(Kg)

85

Ideal Weight(Kg)

74.982

BSA (m^2)

2.05

BMI (kg/m^2)

26.2

Latest HCT (%)

30

Latest Hb (g/dL)

10

Prime Volume

1200

Anesthesia Volume Removed (mL)

0

Total Anesthesia Fluids (mL)

Figure 2:
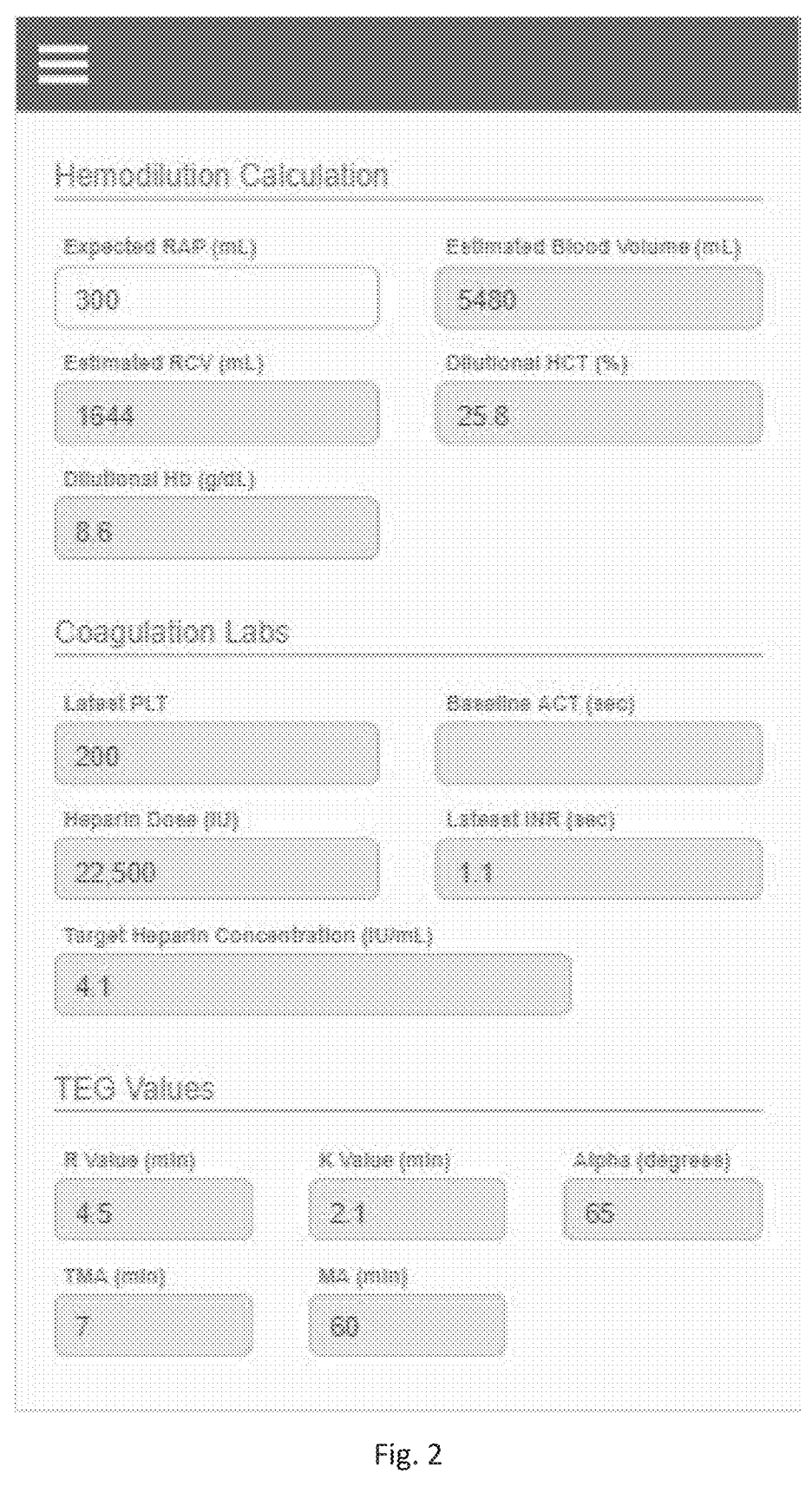

Hemodilution Calculation

Expected RAP (mL)

300

Estimated Blood Volume (mL)

5480

Estimated RCV (mL)

1644

Dilutional HCT (%)

25.8

Dilutional Hb (g/dL)

8.6

Coagulation Labs

Latest PLT

200

Baseline ACT (sec)

Heparin Dose (IU)

22,500

Latest INR (sec)

1.1

Target Heparin Concentration (IU/mL)

4.1

TEG Values

R Value (min)

4.5

K Value (min)

2.1

Alpha (degrees)

65

TMA (min)

7

MA (min)

MONITORING SYSTEM FOR CARE PROTOCOLS

BACKGROUND OF THE INVENTION

The present invention relates broadly to the field of patient monitoring systems and process control tools in healthcare, such as for example, a process control tool that will seek to optimize oxygen delivery during cardiopulmonary bypass, and the like. It can be appreciated that an effective process control tool may require real time data from multiple sources to collect data required to perform advanced calculations automatically, comparing the calculated results to defined process control limits. Unfortunately, there is no current way to write, deploy and evaluate process controls in real time. The present invention can be appreciated in the context of open-heart surgery as an example, but has, as is noted, a broader applicability.

Open heart surgery may be regarded as one of the most important medical advances in the 20th century, and cardiopulmonary bypass has been key to the development of open-heart surgery. The term cardiopulmonary bypass describes technology in which the circumvention of native heart and lungs is achieved with the use of extracorporeal devices. Examples of extracorporeal devices that may be used to circumvent a patient's native heart and/or lungs to provide mechanical means for pumping and oxygenating blood include cardiopulmonary bypass machines and extracorporeal membrane oxygenation (ECMO) machines.

Employing a cardiopulmonary bypass machine to replace the function of a patient's heart and lungs requires constant monitoring of the patient's perfusion, oxygen delivery, and physiological parameters to ensure that the patient's oxygen consumption needs are met by the oxygen delivery provided by the cardiopulmonary bypass machine. If the cardiopulmonary bypass machine is not operated optimally to provide the patient with adequate mechanical perfusion, and/or to provide an oxygen delivery that surpasses the patient's oxygen consumption needs, then increased morbidity and mortality may result from tissue hypoxia due to inadequate oxygen delivery to the patient's tissues and anaerobic metabolism. Insufficient oxygen delivery during cardiopulmonary bypass, due either to excessive anemia, or to low flow (i.e., inadequate perfusion), or both, is associated with postoperative complications or increased post-operative surgical mortality, often due to multi-organ failure including renal and gastrointestinal organ systems. While certain patient parameter's may be measured during cardiopulmonary bypass, such as hematocrit % (HCT), hemoglobin (g/dL), arterial oxygen saturation (%), arterial oxygen tension (mm Hg), etc., despite intraoperative measures taken to maintain adequate oxygen delivery based on these parameters, inadequate oxygen delivery and tissue hypoxia may still occur during cardiopulmonary bypass procedures as evident from postoperative elevated levels of blood lactate levels.

One predictor of elevated lactate levels resulting from tissue hypoxia is the ratio of indexed oxygen delivery ($DO_{2i}$) to indexed carbon dioxide elimination ($VCO_2i$). However, this ratio is a complicated calculation derived from a number of measured variables, from multiple data sources, so its use has been limited to a retrospective clinical outcomes research. Furthermore, there are no systems available that would allow a user to monitor such a complicated clinical predictor in real time and, at the same time, facilitate in the operating room, optimization of one or more complicated clinical predictors to improve patient care. These calculations may require data from multiple sources, making real time calculation impractical in the OR. The collection of data is further complicated due to the various machine languages used for data transmission from the electronic devices.

Monitoring systems for cardiac surgical operations with cardiopulmonary bypass are known. For example, U.S. Pat. No. 10,039,490 to Ranucci, the disclosure of which is incorporated herein by reference, teaches a monitoring system for cardiac operations with cardiopulmonary bypass comprising: a processor operatively connected to a heart-lung machine; a pump flow detecting device connected to a pump of the heart-lung machine to continuously measure the pump flow value and send it to the processor; a hematocrit reading device to continuously measure the blood hematocrit value and to send it to the processor; a data input device to allow the operator to manually input data regarding the arterial oxygen saturation and the arterial oxygen tension; computing means integrated in the processor to compute the oxygen delivery value on the basis of the measured pump flow, the measured hematocrit value, the preset value of arterial oxygen saturation, and the preset value of arterial oxygen tension; and a display connected to the processor to display in real time the computed oxygen delivery value. There is a need in the field of cardiopulmonary bypass operations, and other similar operations and/or medical-surgical intensive care settings, for a system and method that can be used to operationalize any process control including to collect data from multiple sources, calculate, simulate, and monitor complicated calculated indicators of adequate oxygen delivery and oxygen consumption in real time to prospectively make better clinical decisions. More generally, there is a need in the field of medicine and surgery for a system and method that can be used to calculate, simulate, and monitor complicated indicators of medical interventions, patient outcome and survival, namely, clinically relevant parameters for a patient, in real time, wherein each of these medical interventions and clinical parameters constitute complicated functions of multiple data input parameters and are useful in helping clinicians prospectively make better clinical decisions and operationalize any process control in the most compliant manner.

SUMMARY OF THE INVENTION

Broadly, the present invention is directed to a monitoring system that will allow clinicians to generate, operationalize and get feedback on any process control in real time. The system can include a clinical parameter calculation-simulation-monitoring system, such as may be used to calculate, simulate and/or monitor complicated clinical parameters, such as those that are functions of multiple measured variables. The present invention may be used, for example, for an oxygen delivery and consumption monitoring system that facilitates the calculation, simulation, and/or monitoring of oxygen delivery and oxygen consumption for a patient during cardiac bypass surgeries, and like surgical and/or medical situations in which the calculation, simulation, and/or monitoring of oxygen delivery and oxygen consumption is desired. Specifically, the present invention can apply to a perfusion monitoring system that facilitates the calculation, simulation and/or monitoring of a patient's hematocrit or hemoglobin values during cardiac bypass surgeries, and like surgical and/or medical situations in which the calculation, simulation and/or monitoring of a patient's perfusion status is required.

The invention is directed to a monitoring system for care protocols, wherein the system comprises a plurality of sensors operably connected to electronic devices to input data from a patient to an interface, said sensors being disposed to measure critical values from a patient; an interface for receiving input data and allowing users to define process control limits and when appropriate change these limits of a process control in real time, as appropriate for the care of the specific patient; a means for authorized practitioners to formally document the decision to deviate from a medical facility defined protocol or the specific patient care plan; a processor operably connected to the interface to date stamp and receive, agnostically, data signals corresponding to received data input pertaining to one or more input parameters, wherein specific data values collected from the multiple data sources may be used in more than one output calculation formula, the processor calculates one or more output values based on the one or more input parameters and compares said output values to said critical values to determine in real time whether said output values are outside an acceptable range; and input means for setting critical values for a patient, ranges of critical value, and alarm points when the critical values are outside of the ranges by providing appropriate defined notifications/prompts and/or recommended actions in real time; said interface configured to receive data input pertaining to one or more input parameters selected from the group consisting of patient input parameters, perfusion input parameters, oxygen delivery input parameters, oxygen consumption input parameters, carbon dioxide production input parameters, narcotic input parameters, blood pressure input parameters, and other critical patient input parameters, and combinations thereof; wherein the interface includes a manual input for at least one or more input parameters by a user and a machine input configured to receive sensor-derived input from one or more sensors; and wherein the system is operable to perform one or more functions directed to calculating and monitoring critical steps or values for a patient and enables the output values for monitoring or for display, in real time, including the output values calculated by the processor, and the range of critical values.

In other examples of the use of the system in accordance with the present invention, clinicians will be able to define groups of patients, define interventions to be applied to groups at various phases of care, define who should be alerted and how, and see performance in real time. For example, process control to reduce narcotic use during surgery and identify which patients process control should apply to, identify specific interventions for pre/intra/post op phases, define changes to case flow (documentation), alerts, notifications and verifications as applicable, define escalation pathways, define reporting requirements. Once operationalized, supervising clinicians will have full visibility to entire process including deficiencies and deviations from expected course in real time. Different alerts based on different clinical roles Another use of the system in accordance with the present invention would be in blood pressure management. The system would define which patients should be in blood pressure management process control, define specific interventions that should apply to different phases of care (such as, early labor, post-partum, and the like), and see compliance and be alerted to exceptions and deviations from expected course in real time. Different alerts based on different clinical roles.

Another use of the present system would be for control, such as when a ventilator is in use and in the ventilator weaning, the system will define which patients should be weaned from ventilator support, define step wise weaning approach, and define when patients are ready for next step in weaning or identify those who are failing and should be replaced on original support in real time. There can be different alerts based on different clinical roles.

Thus, the present invention has the ability to define, operationalize, and get feedback in real time in any care area or patient population, which is clinician defined.

BRIEF DESCRIPTION OF DRAWINGS

The foregoing and other features and advantages of the present invention will become apparent to those skilled in the art to which the present invention relates upon reading the following description with reference to the accompanying drawings, in which:

FIGS. 1-4 are front view of a monitoring device showing a screen displays of the patient's vitals, the hemodilution calculation, the protamine risk and vital settings, and the intra-Op Cockpit in normal state;

DETAILED DESCRIPTION OF THE INVENTION

Figure 3:
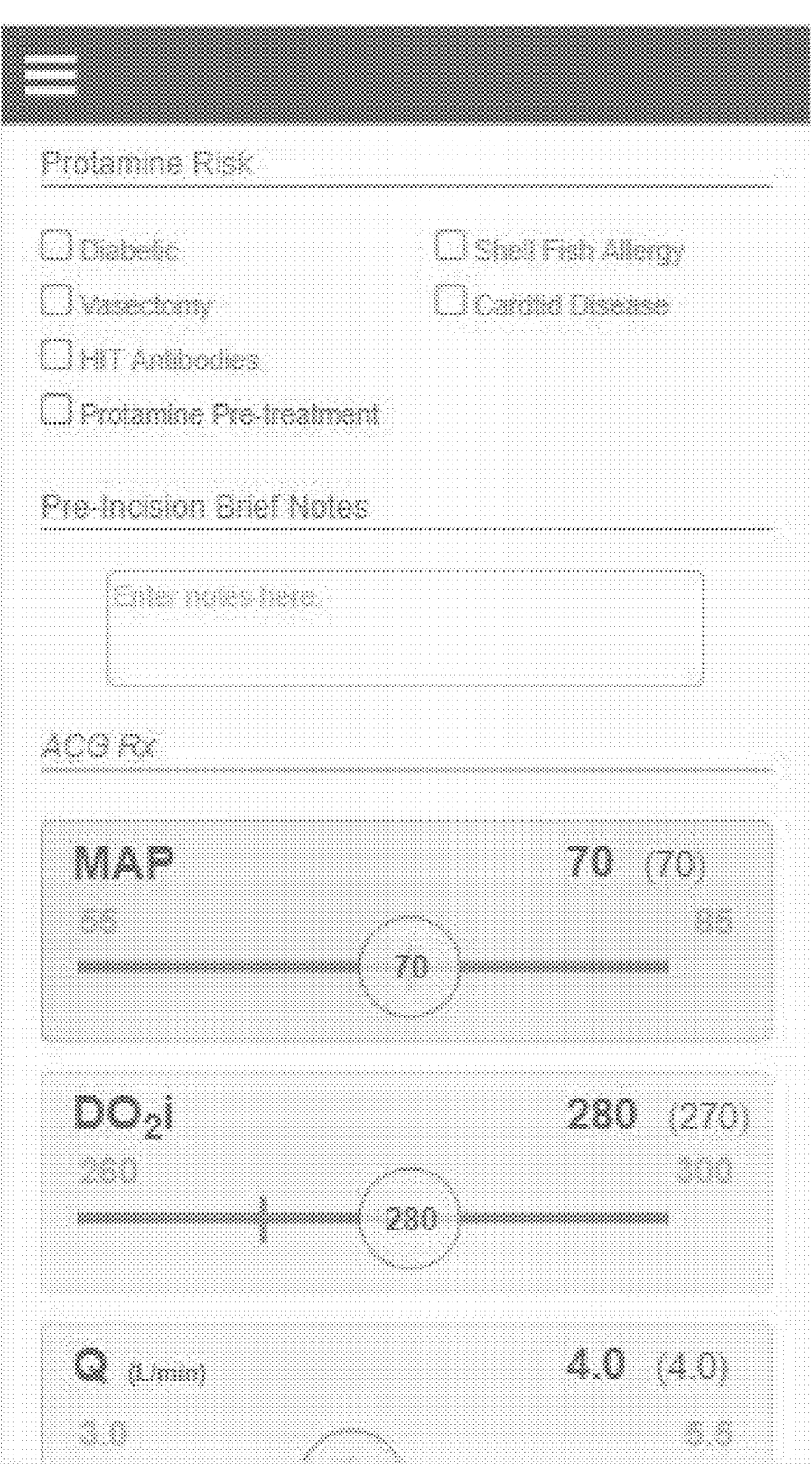

The present invention is directed to a monitoring system for medical patient care protocols, such as surgical operations, that is capable of writing, operationalizing and providing feedback on any process control, in real time. To accomplish this the system is capable of collecting information from any number of electronic devices including medical devices and manual entries. The data is collected, time stamped at time of data collection, stored, translated to the appropriate machine language, transmitted to the data storage repository, using applicable calculation algorithm, and providing the required notification and/or prompt to the medical practitioner(s) requiring notification. The system performance allows this series of activities to be accomplished in milliseconds.

The monitoring system of the present invention comprises a plurality of sensors operably connected to electronic devices to input data from a patient to an interface for receiving input data and allowing users to write process controls and change elements of a process control in real time; a processor operably connected to the interface to receive data signals corresponding to the received data input pertaining to the one or more input parameters, wherein specific data values collected from the multiple data sources may be used in more than one output calculation formula.

The interface is configured to receive data input pertaining to one or more input parameters, including patient input parameters, perfusion input parameters, oxygen delivery input parameters, oxygen consumption input parameters, carbon dioxide production input parameters, narcotic input parameters, blood pressure input parameters, and other critical patient input parameters and the interface includes a manual input of at least one or more input parameters by a user and a machine input configured to receive sensor-derived input from one or more sensors; and wherein the system is operable to perform one or more functions directed to calculating and monitoring critical steps or values for a patient and enables the output values for monitoring or for display, in real time, including the output values calculated by the processor, and the range of critical values. The sensors are disposed to measure critical values from a patient The system of the present invention includes means to connect to all medical devices to facilitate collection of data as fast as the devices can output data, means to integrate to any available health information system, including electronic health records, means to document and facilitate manual user input, means to leverage published simple computations to calculate clinician required values as needed, a processor operably connected to receive and process the collected data in real time, to execute clinician generated process controls, means to dynamically change documentation requirement to simplify and execute process control as needed, means for providing notifications, verifications, and guidance alerts, and monitor display means to allow users to see which process controls are operational, exceptions, alerts etc. and provide full visibility of what is going on in patient populations at all times and means for real time reporting.

The present invention is focused on the care giver defining the patient care plan (prescription) with or without the formulas. This is true regardless of the specific care plan or area. With the present invention the use of closed loop interoperability, which is known in the industry, is not required. With the present invention interoperability as defined by the industry and FDA is never required. The tool provides a means to control the processes and compliance with practitioner directed care without the limitations of medical device interoperability.

The processor calculates one or more output values based on the one or more input parameters and compares said output values to said critical value to determine in real time whether the output values are outside the acceptable range. The input means allows for setting critical values for a patient, ranges of critical value, and alarm points when the critical values are outside of the range by providing appropriate defined notifications and prompts and/or recommended actions in real time. These calculations are known in the industry and are made using formulas known in the industry and can be done using the processor. By comparison of the input and output values, it is determined that the output values are outside of the acceptable range.

The present invention provides a way to write, deploy and evaluate process controls in real time. The process controls will be clinician defined and can be editable on the fly. The process can include any interventions including medications or procedures and can also indicate clinical guidance that can be used to mitigate negative patient events. The present invention can span care areas and phases of care, can include multiple care teams, can provide clinical role specificity and manage hand-offs, such as transitions of care. The present invention will provide for exceptions/deviations from expected care and patient course to be viewable in real time. Thus, compliance reports available at defined times (e.g. case end) to "close loop". The present invention incorporates mobile tools, such as smart phones, tables, etc., that augment clinical workflows.

The present invention is achieved by connecting disparate data sources (devices, electronic health records (EHR) etc.) so that process controls can be implemented and visualized in real time, providing a simple user interface (UI) for clinicians to write their own process controls, allowing clinicians to change elements of a process control in real time, allowing clinicians to indicate whether is process control is relevant in real time, sorting patients into risk groups or other categories in real time, matching groups of patients at risk/or patient categories with risk or group specific interventions, and incorporating decision support elements and documentation tools to dynamically indicate when specific interventions are due based on patient risk/categories to make it easy for clinicians who are executing the process control to understand when something is due proactively, and when something is past due. Thus, the present invention exposes compliance with a process control or deviation from expected course in real time by closing the loop in real time so that process improvement can occur.

The programed computer will receive data from various sources, such as medical devices for monitoring and/or treating a patient. Monitored data can comprise physiological data elements, video data elements, and audio data elements. Once the data is received, it is date stamped, and stored. The present invention allows the data to be collected agnostically. By agnostically, it is meant that the data is collected from various sources, equipment, instruments, and/or sensors without regard to the language in which it is transmitted, and/or is generalized so that it is interoperable among various systems. So, the system of the present invention does not require a match with the data source to be functional and can accommodate various data sources.

The data which may need to be translated or converted to the machine-language of the programed computer is translated. This means translating data received from any electronic source to the data storage language of the computer, and, in turn, translating from the data storage to the language of the receiving electronic source. This allows the hospital to utilize any number of suppliers and/or device models within the interoperability environment. This eliminates the need to buy new equipment just to achieve interoperability. The system will allow access to all relevant patient data from all applicable sources as discussed above and a means to store accurately, timely and completely all relevant data regarding patient care and patient response/outcome. If translation is unnecessary, the data is stored, preferably in a cloud storage, which provides remote access to the data. The data is then evaluated for the accuracy of the data and that is verified. In response to a request for data transfer to a target device, the applicable data is collected per the data mapping requirements. If data translation is needed for the target device, evaluation and translation are done. Then, the data is transmitted to the target device and the accuracy is verified.

As an example, data can be expressed in many machine-language instructions. Since there are many machine-languages, as is known in the art, each device and operating system functions in its chosen machine-language. The present invention senses the machine-language in which the data is presented and translates it into the machine-language employed by the present invention. The machine-language employed by the present invention is not critical and is one known in the art. So, it is only a matter of translating the machine-language of the data received to that which will function in the method and system of the present invention. In turn, when data is transmitted to an electronic source, it is translated into the machine-language of that source.

The present invention allows for the acquisition of data from multiple disparate sources, consolidation of all information within a unified view with all data time synchronized at time of collection, running process controls and workflows, and delivering actionable insights to specific users in real time, i.e., the actual time during which an event occurs. Since data is being acquired in real time, the time synchronization is required to accurately align the data from the various sources of information. The internal clocks of the various sources are not in agreement and may not be provided as part of the data provided by the device. Therefore, the need to synchronize the data to the time collected rather than use the various electronic source times, if available. This allows the data from multiple sources to be presented on the same screen. This allows for an accurate representation and display of the alignment of patient interaction with the patient's response, which is required for an informed assessment of patient response to patient care activities.

Data from various sources, including monitored data elements from any electronic device, such as medical devices for monitoring and/or treating a patient, can comprise physiological data elements, video data elements, and audio data elements. Once the data is received, it is date stamped, and stored. Data which is received may need to be translated or converted from the machine-language in which it is sent to the machine-language of the processor of the present invention. If the data which needs to be translated or converted to the machine-language of the processor of the present invention, is translated. If translation is unnecessary, the data is stored, preferably in a cloud storage, which provides remote access to the data. The data is then evaluated for the accuracy of the data and that is verified. In response to a request for data transfer to a target device, the applicable data is collected per the data mapping requirements. If data translation is needed for the target device, evaluation and translation are done. Then, the data is transmitted to the target device and the accuracy is verified.

The present invention provides an effective process control tool by requiring that real time data from multiple sources be collected so that the calculations can be done automatically and the calculated results can be compared to defined process control limits. When calculated values indicate that the value is not within specified ranges, the notification and prompt rules are activated, and appropriate individuals are made aware of the condition.

EXAMPLE

Converting a pre-incision brief during cardiac surgery into a process control that is dynamically executed in real time, with full transparency.

Traditionally, elements of patient's care during CPB are verbally discussed by Surgeon and Perfusionist during pre-incision brief. E.g. Surgeon instructs Perfusionist to maintain perfusion within certain settings including pump flow, hemoglobin and oxygen delivery/SVO2. Surgeon has no ability to see perfusion course compared to desired goals while case in progress. Surgeon has no ability to evaluate perfusion course compared to goal in summary at case end.

With the present invention, the Perfusionist will enter all surgeon instructions into a mobile pre-incision briefing tool. The instructions will be converted to an advanced clinical guidance prescription in real time. The surgeon will have full visibility into compliance with the advanced clinical guidance prescription in real time while case in process. Surgeon will also be able to view compliance summary at the cases end in any format, including mobile.

Definitions and Abbreviations

HCT: hematocrit (%)
Hb: hemoglobin (g/dL)

CPB: cardiopulmonary bypass
T: temperature (° C.)
$VO_2$=oxygen consumption (mL/min)
$VO_2$i=oxygen consumption indexed (mL/min/m$^2$)
$DO_2$=oxygen delivery (mL/min)
$DO_2$i=oxygen delivery indexed (mL/min/m$^2$)
$O_2ER$=oxygen extraction rate (%)
$VCO_2$=carbon dioxide production (mL/min)
$VCO_2$i=carbon dioxide production indexed (mL/min/m$^2$)
Ve=ventilation (L/min)
$eCO_2$=exhaled carbon dioxide (mmHg)
AT=anaerobic threshold
LAC=lactates
Qc=cardiac output (mL/min)
IC=cardiac index (Qc/m$^2$), (mL/min/m$^2$)
Qp=pump flow (mL/min)
IP=pump flow indexed (Qp/m$^2$), (mL/min/m$^2$)
$CaO_2$=arterial oxygen content (mL/dL)
Cv $O_2$=venous oxygen content (mL/dL)
$PaO_2$=arterial oxygen tension (mmHg)
$PvO_2$=venous oxygen tension (mmHg)
a=arterial
v=venous
Sat=Hb saturation (%)

The following equations are applied to implement the monitoring system according to the invention:

$$VO_2 = Qc \times (CaO_2 - CvO_2) \text{ in a normal circulation} \tag{1}$$

$$VO_2 = Qp \times (Ca\ O_2 - CvO_2) \text{ during } CPB \tag{2}$$

$$DO_2 = Qc \times CaO_2 \text{ in a normal circulation} \tag{3}$$

$$DO_2 = Qp \times CaO_2 \text{ during } CPB \tag{4}$$

$$O_2ER = VO_2 / DO_2\ (\%) \tag{5}$$

$$Hb = HCT / 3 \tag{6}$$

$$CaO_2 = Hb \times 1.36 \times Sat(a) + PaO_2 \times 0.003 \tag{7}$$

$$CvO_2 = Hb \times 1.36 \times Sat(v) + PvO_2 \times 0.003 \tag{8}$$

$$VCO_2 = Ve \times eCO_2 \times 1.15 \tag{9}$$

The present system can be employed, for example, with a heart-lung machine, or as a cardiac bypass system, or as a cardiopulmonary bypass system, and which includes cardiopulmonary bypass (CPB) systems, minimal extracorporeal circulation (MECC) systems, extracorporeal membrane oxygenation (ECMO) systems (respiratory and cardiac), and pump assisted lung protection (PALP) systems) includes an oxygen delivery and consumption calculation-simulation-monitoring system, as well as a venous reservoir, a blood pump and an oxygenator. Such systems are well known and therefore have not been illustrated.

Such systems have blood sensors which measure blood oxygenation parameters $SaO_2$, $PaO_2$, etc., pertaining to the amount of oxygen carried by the blood. A flow meter may be provided to measure the flow rate of blood exiting the blood pump and to input blood flow rate data Qp to the calculation-simulation-monitoring system. A $CO_2$ sensor or capnograph may capture exhaled carbon dioxide ($expCO_2$) data which is continuously measured and input into the calculation-simulation-monitoring system. A hematocrit (HCT) sensor may be placed on the venous or arterial side of the blood flow circuit to measure deoxygenated blood flowing from the cavoatrial cannula. Alternatively, the HCT sensor may be a non-invasive hemoglobin (Hb) sensor. Either HCT data or Hb data can be continuously input to the monitoring system.

The monitoring system includes an interface comprising a manual interface portion and a machine interface portion. The interface is operably connected to provide data input to a programed processor, which employs the data in calculations of output values indicative of the patient's condition, or of output values simulating outcomes of hypothetical or planned clinical intervention. The processor is connected to a display assembly, which is used to display output values calculated by the processor, and to a memory assembly that is used to store output values and non-outputted values calculated by the processor. The memory assembly includes both RAM and ROM components, and/or other devices suitable for data storage. In accordance with an embodiment of this disclosure, processor is a general computer, but the processor may be an embedded system with particular dedicated functions (i.e., such as those described herein) within the larger electrical system of the calculation-simulation-monitoring system.

The manual interface portion is configured so that a user manually inputs data into user interface to populate the calculation-simulation-monitoring system. For example, certain data pertaining to a patient are substantially static data with respect to the cardiopulmonary bypass procedure to be performed. Examples of such static patient data includes patient morphological data such as height and weight, which will not substantially change during the cardiopulmonary bypass procedure. Such static data pertaining to the patient at the start of the cardiopulmonary bypass procedure may be referred to as patient input parameters. Thus, in accordance with this disclosure, static data constitutes data collected before, or at the beginning of a medical and/or surgical procedure and constitutes data that does not change appreciably during the course of the medical and/or surgical procedure.

Other static data that a user may input via the manual interface portion of the interface include perfusion input parameters such as the patient's pre-cardiac bypass blood volume per unit weight, and the patient's pre-cardiac bypass hematocrit. These perfusion input parameters pertain to the patient's starting condition at the beginning of the cardiopulmonary bypass procedure. While hematocrit, for instance, may change during the cardiopulmonary bypass procedure, its starting value at the beginning of the procedure does not. Consequently, it constitutes data that a user may input manually into the system via the manual interface portion.

Figure 4:
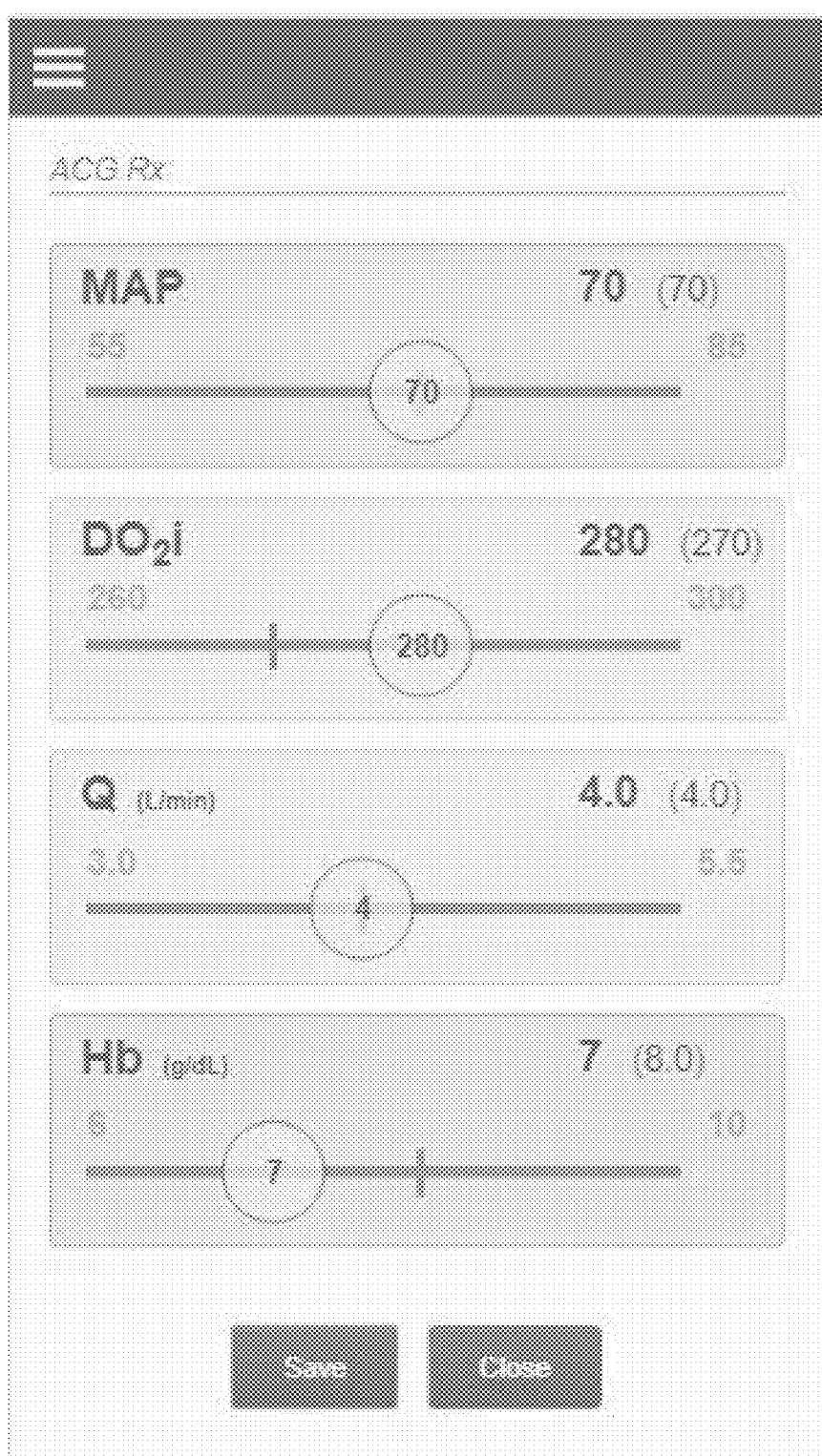

As illustrated in the drawings, in FIG. 1 shows a method a clinician could use to enter a process control, such as, the data on a patient (e.g., height, weight, and age) into the system to define the controls that a clinician can apply to a healthcare process control. In this example, a pre-incision brief is shown. Next, as seen in FIG. 2, a simple calculation, such as, the hemodilution calculation algorithm is automatically performed based upon the patient data entered in FIG. 1. Clinicians can use data from multiple sources in a consolidated format as part of their process control. FIG. 2 shows an example of derived parameters (HCT) computed using a simple equation from parameters entered by clinicians as well as parameters imported from ancillary systems (TEG values) connected to this invention via interfacing. Then, as seen in FIG. 3, the clinicians can dynamically alter the threshold of a previously entered process control, such as setting the desired oxygen delivery components, as shown. The values continue to be displayed in the intra-Op Cockpit (i.e., the intra-operative information capture system of the anesthesia cockpit) in FIG. 4, in a normal state. FIGS. 3 & 4 are examples of parameters that can be used by clinicians to trigger a process control(s), and process control thresholds that can be dynamically altered by clinicians. FIGS. 3 and 4 show an example of parameters that can be checked by a clinician, and how various prescribed parameters of a process control to optimize oxygen delivery can be modified on the fly.

Figure 5:
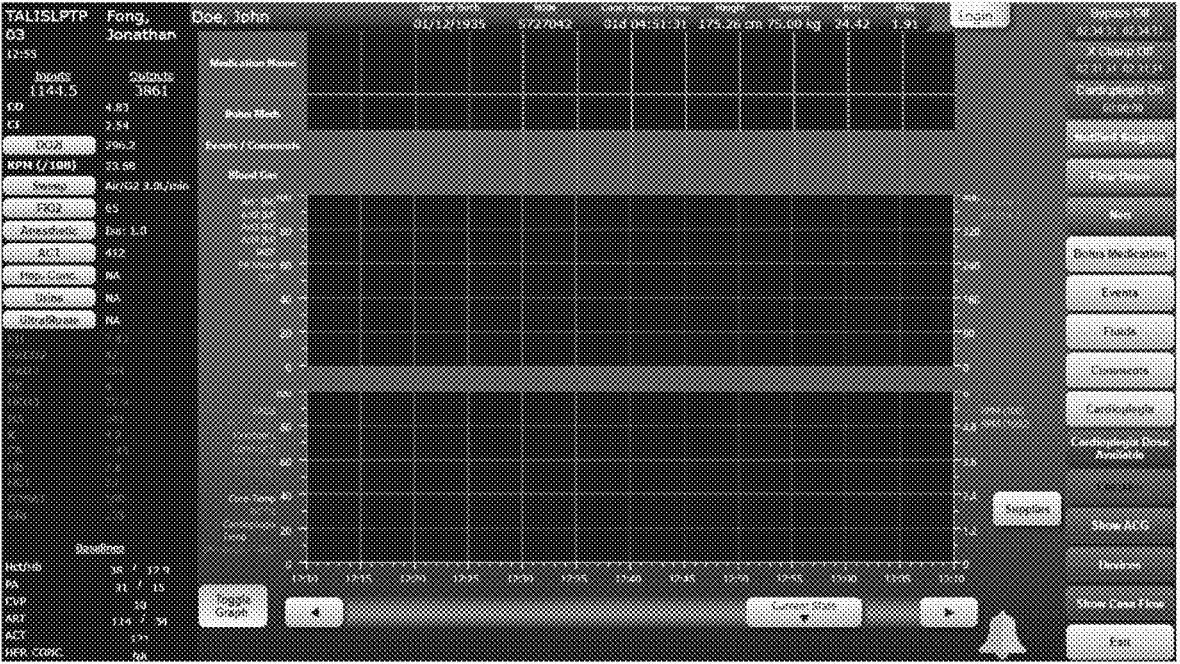
FIGS. 5-8 are front views of a monitoring device showing a screen display of the patient's vitals before, during and after an operation.
Figure 6:
Figure 6:
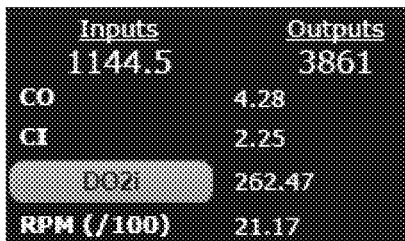

In FIGS. 5 and 6 are examples of how compliance to a process control can be viewed in real time at the point of care. The figures show how a process control to optimize oxygen delivery during bypass can be visualized on a perfusionist documentation tool. FIG. 6 shows intra-op cockpit in low Q state.

Figure 7:
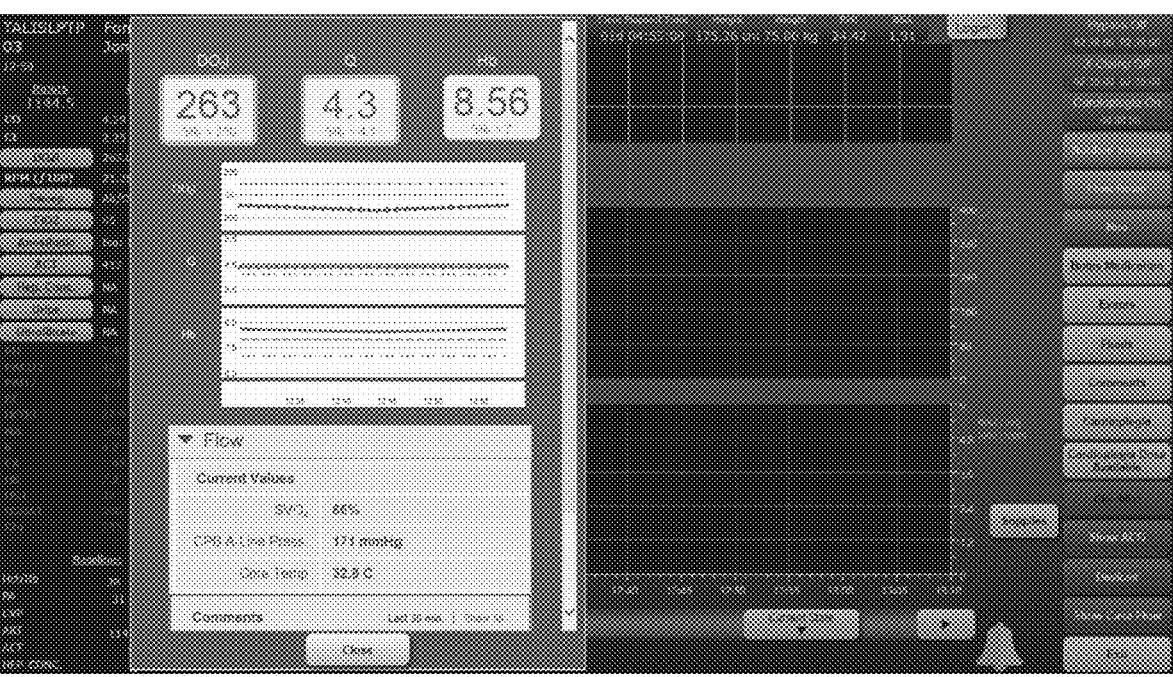
Figure 7:
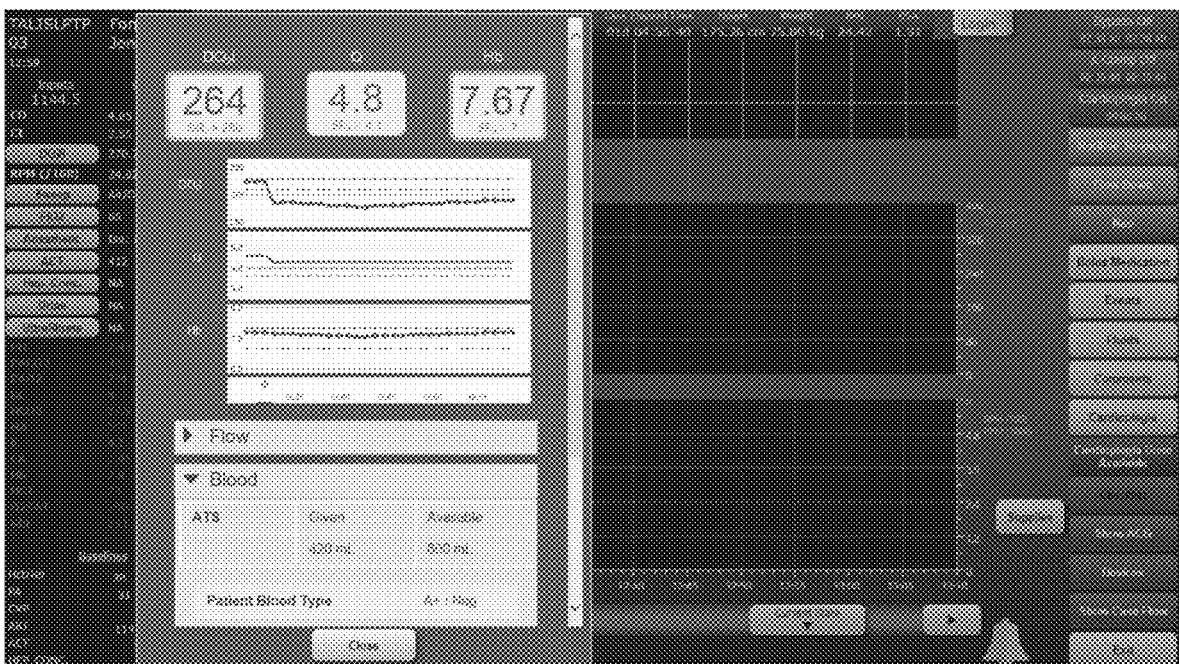
Figure 8:
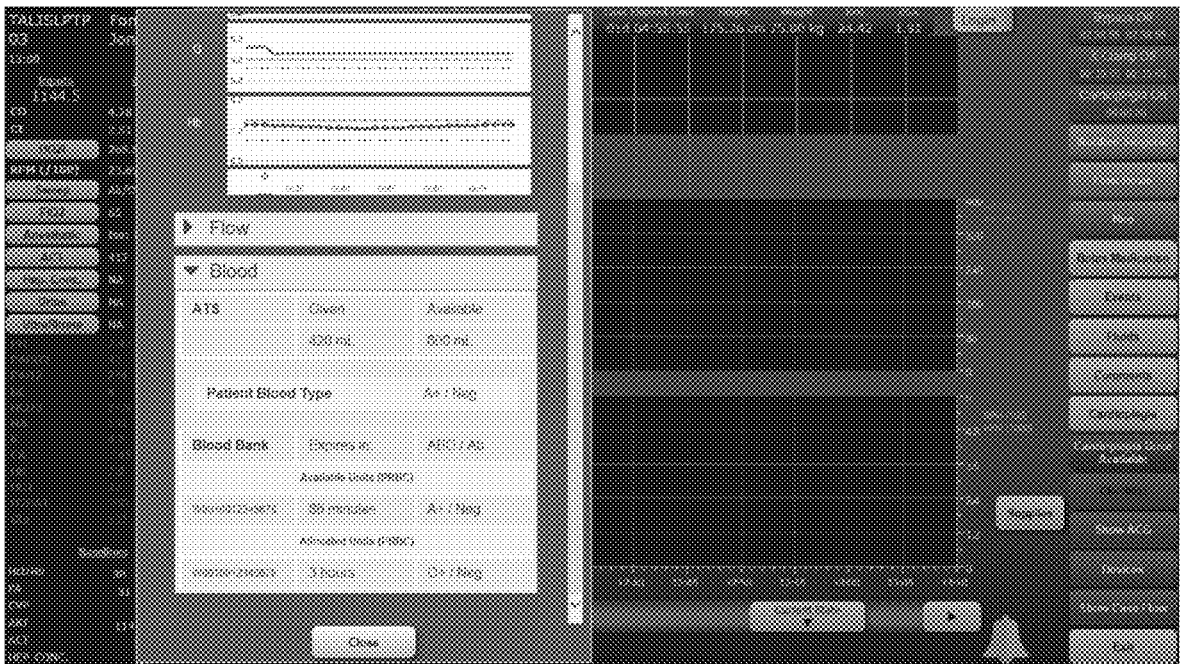
Figure 9:
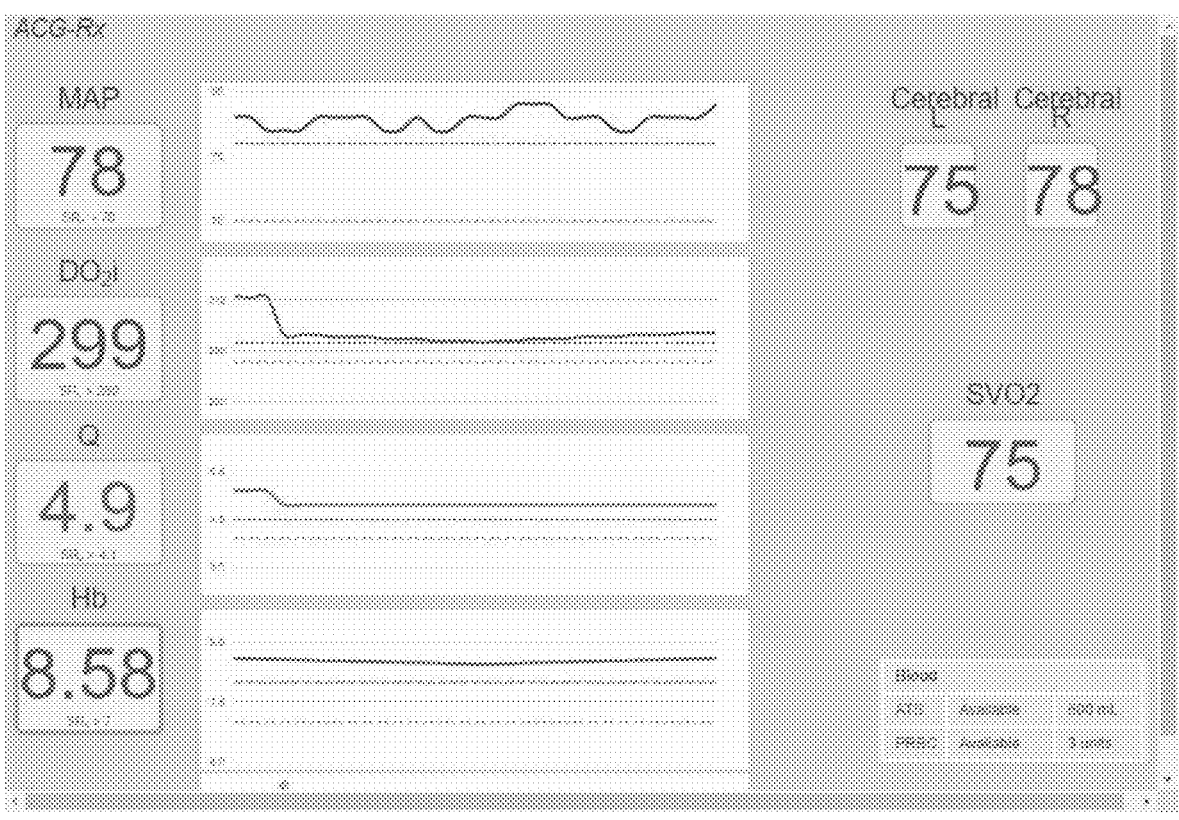
FIG. 9 is a front view of a monitoring device showing a screen display of the patient's vitals as part of a prescription compliance report.
Figure 10:
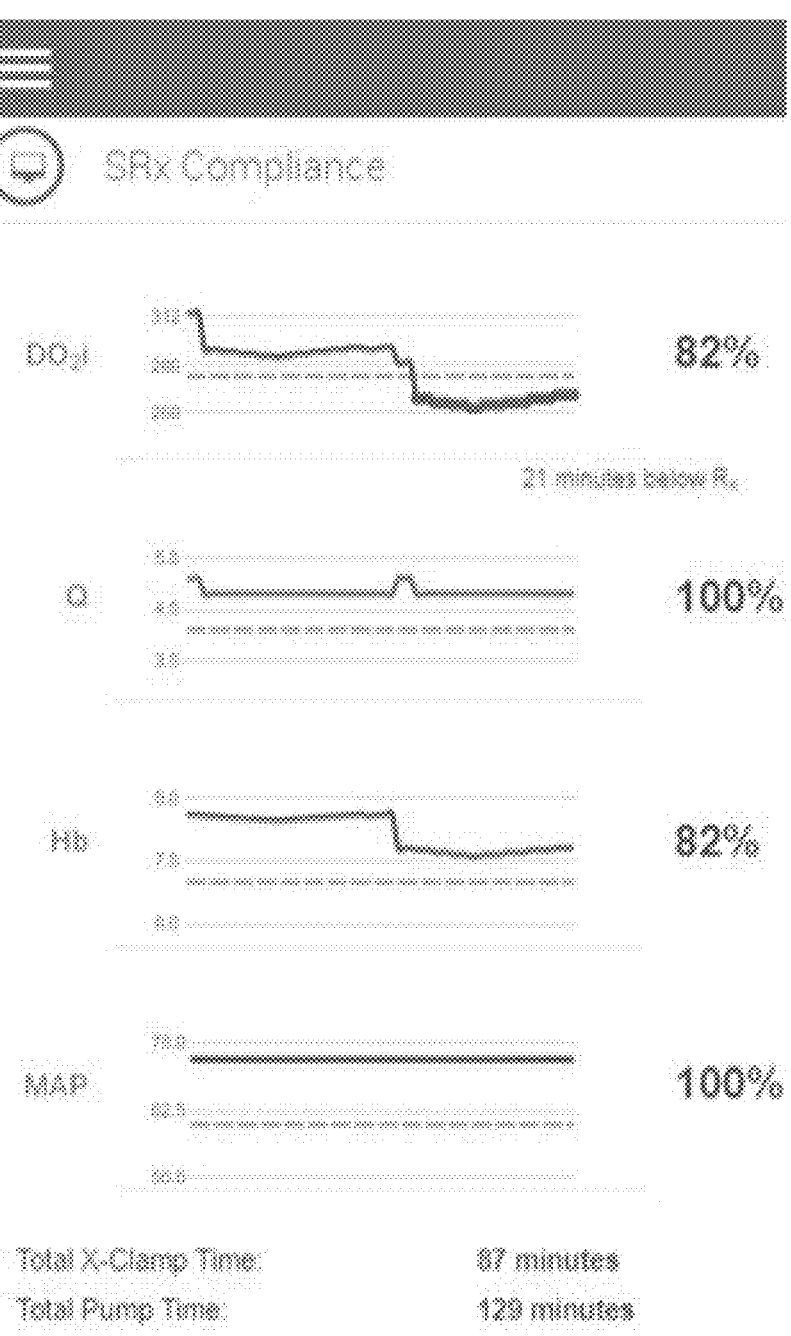
FIG. 10 is a front view of a monitoring device showing a screen display of the patient's vitals throughout an operation and presented in graphical form.

FIGS. 7, 8, 9, and 10 are examples of how a deviation from prescribed care within a process control point value can be identified and classified at the point of care. FIG. 7 shows values within prescribed control values in low Q state. FIGS. 8, 9, and 10 show a deviation of prescribed control can be shown in real time at the point of care. For example, a deviation from prescribed oxygen delivery is highlighted, along with a drill down view of additional information to be presented as defined by the process control. FIG. 8 shows a surgeon intra-op dashboard, and FIG. 9 shows a prescription compliance report.

FIG. 10 is an example of how aggregate compliance with a process control can be viewed at end of a care episode. In this example, perfusionist compliance with prescribed Oxygen Delivery, Pump Flow, Hemoglobin, and Mean Arterial Pressure are shown, along with additional information that quantifies non-compliance.

Although the invention has been presented by the example of the drawings, it is much broader. It is a tool that allows users to write, deploy and get feedback on process controls in real time. Targeted oxygen delivery for perfusion is just one example.

Although the invention has been described in detail with reference to particular examples and embodiments, the examples and embodiments contained herein are merely illustrative and are not an exhaustive list. Variations and modifications of the present invention will readily occur to those skilled in the art. The present invention includes all such modifications and equivalents. The claims alone are intended to set forth the limits of the present invention.

What is claimed is:

1. A monitoring system, comprising:

a plurality of sensors configured to sense sensors input data from a patient, each of the sensors being operably connected to a corresponding electronic device;

a sensor interface coupled to the sensors and configured to receive from the sensors input data and to allow users to define process control limits and, when appropriate, to change these process control limits in real time;

an authorized user interface permitting authorized practitioners to input patient care parameters corresponding to a patient care plan; and a processor operably connected to the plurality of sensors, wherein the processor is configured to:

first, sense a machine language of each of the input data;

after sensing the machine language of each of the input data, determine, based on the sensed machine language of each of the input data, whether each sensed machine language differs from a first machine language of the processor;

in response to determining that the machine language of a given input datum differs from the first machine language of the processor, translate the machine language of the given input datum to the first machine language; and in response to determining that the machine language of the given input datum is the same as the first machine language, not translate the given input data and store the given input data in the first machine language, wherein the processor is operably connected to the sensor interface to date stamp data signals corresponding to the sensors input data, the processor calculating at least one output value including at least one of a hematocrit and a hemoglobin level based on the sensors input data and comparing the at least one output value to the patient care parameters to determine in real time whether the at least one output value is acceptable based on the patient care plan.

2. A system for real time calculation of patient care parameters of a patient, comprising:

a plurality of sensors detecting data corresponding to patient care decisions, the sensors including a first sensor receiving first data of the data and a second sensor receiving second data of the data, wherein a first form of the first data is incompatible with a second form of the second data;

a patient care device;

a memory storing parameters relevant to a course of treatment for the patient along with a desired range for at least a first parameter of the parameters based on the course of treatment; and a processor coupled to the sensors and configured to:

first, receive the data from the sensors;

second, sense the first and second forms of the first and second data, respectively;

third, compare each of the sensed first and second forms to a form used by the processor; and fourth, (a) in response to determining that the first form differs from the form used by the processor, translate the first data into one of (i) the second form and (ii) the form used by the processor into which the second data has also been translated; and, (b) in response to determining that the first form is the form used by the processor, not translate the first form, the processor being configured to combine the first and second data to determine whether the first parameter of the parameters stored in the memory that is based on the data represented by the first and second data is in the desired range.

3. The system of claim 2, wherein the first data is one of a hematocrit or hemoglobin value, and the second data is a pump flow rate value and third data of the data from a third sensor of the sensors is an arterial oxygen saturation value, the processor translating at least one of the first, second and third data so that the processor can combine at least one of the first, second, and third data to calculate an indexed oxygen delivery value.

4. The system of claim 3, wherein the memory includes a stored range for the indexed oxygen delivery value and wherein the processor is configured to compare the calculated indexed oxygen delivery value to the stored range for the indexed oxygen delivery value.

5. The system of claim 4, further comprising an alarm triggered by the processor when the calculated indexed oxygen delivery value is outside of the stored range of delivery value stored in the memory.

6. The system of claim 4, further comprising a display operably coupled to the processor, the display configured to display, in a first window, the calculated indexed oxygen delivery value, and in a second window values of physiological parameters of the patient in real time during a care episode, wherein the processor is further configured to display on the display a compliance report at an end of the care episode.

7. The system of claim 2, further comprising an interface configured to receive input provided by a user relating to the course of treatment or the desired range for the first parameter.

8. The system of claim 2, wherein the first data includes physiological data, the second data includes video data and third data of the data from a third sensor of the sensors includes audio data, and wherein the processor is configured to not translate the first form of the physiological data in response to detection that the first form of the physiological data is the form used by the processor, translate the form of the video data into the form used by the processor in response to detection that the second form is different from the form used by the processor, and translate the audio data into the form of the processor in response to detection that the the a third form of the audio data is different form the form used by the processor.

9. The system of claim 2, wherein the first data is time stamped by the processor upon receipt.

10. The system of claim 2, wherein the processor is coupled to the device providing treatment to the patient, the processor being configured to translate instructions for the device into a language compatible with the device.

11. The system of claim 10, wherein the processor is configured, when connected to the device, to identify a machine language compatible with the device.

12. The system of claim 9, wherein the processor is configured to interface with internal clocks of the first and second sensors to synchronize the first and second data in a consistent common time frame.

13. The system of claim 6, wherein the compliance report displays additional information that quantifies non-compliance of indexed oxygen delivery.

14. The system of claim 1, wherein, in response to determining that the machine language of the given input datum is the same as the first machine language, the processing is configured to store the given input data in cloud storage.

15. The system of claim 2, wherein, when the first form is not translated when the first form is the form used by the processor, the first data is stored in cloud storage.

16. The system of claim 2, wherein, in response to a request for data transfer to a target device, the processor is configured to perform machine language evaluation and selective translation of the data relative to a machine language of the target device.

* * * * *